United States Patent
Boege

(10) Patent No.: US 6,839,179 B2
(45) Date of Patent: Jan. 4, 2005

(54) IMAGING SYSTEM AND METHOD FOR REDUCTION OF INTERSTITIAL IMAGES

(75) Inventor: Steven J. Boege, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/436,415

(22) Filed: May 12, 2003

(65) Prior Publication Data
US 2003/0210469 A1 Nov. 13, 2003

Related U.S. Application Data

(60) Provisional application No. 60/379,483, filed on May 10, 2002.

(51) Int. Cl.[7] .......................... G02B 27/10; G02B 21/18
(52) U.S. Cl. ....................... 359/626; 359/372; 359/618; 359/663; 359/740
(58) Field of Search ................................ 359/372, 373, 359/656, 626, 784, 657–661, 809, 619, 326, 328, 618, 634, 663, 740

(56) References Cited

U.S. PATENT DOCUMENTS

| 5,354,977 | A | | 10/1994 | Roustaei |
| 5,621,547 | A | * | 4/1997 | Loiseaux et al. ............ 359/15 |
| 5,734,155 | A | * | 3/1998 | Rostoker ................. 250/208.1 |
| 5,757,482 | A | | 5/1998 | Fuchs et al. |
| 5,871,628 | A | | 2/1999 | Dabiri et al. |
| 5,876,946 | A | | 3/1999 | Burbaum et al. |
| 5,948,231 | A | | 9/1999 | Fuchs et al. |
| 5,958,202 | A | | 9/1999 | Regnier et al. |
| 6,054,034 | A | | 4/2000 | Soane et al. |
| 6,074,827 | A | | 6/2000 | Nelson et al. |
| 6,100,535 | A | | 8/2000 | Mathies et al. |
| 6,176,962 | B1 | | 1/2001 | Soane et al. |
| 6,473,239 | B1 | * | 10/2002 | Volcker et al. ............ 359/624 |
| 6,567,219 | B1 | * | 5/2003 | Tanaka .................... 359/624 |
| 2002/0030894 | A1 | | 3/2002 | Volcker et al. |
| 2002/0034015 | A1 | * | 3/2002 | Cho et al. .................... 359/629 |
| 2002/0085288 | A1 | * | 7/2002 | Dewald et al. ............ 359/626 |
| 2002/0114079 | A1 | * | 8/2002 | Ohuchi et al. ............. 359/619 |

FOREIGN PATENT DOCUMENTS

| GB | 2 351 556 A | 1/2001 |
| WO | WO 01/86240 A2 | 11/2001 |

OTHER PUBLICATIONS

PCT International Search Report dated Aug. 15, 2003.

* cited by examiner

*Primary Examiner*—Georgia Epps
*Assistant Examiner*—M. Hasan

(57) ABSTRACT

An optical imaging system with a first imaging lens, a field stop, and a second imaging lens configured to reduce the amount of dead space between images of samples.

10 Claims, 8 Drawing Sheets

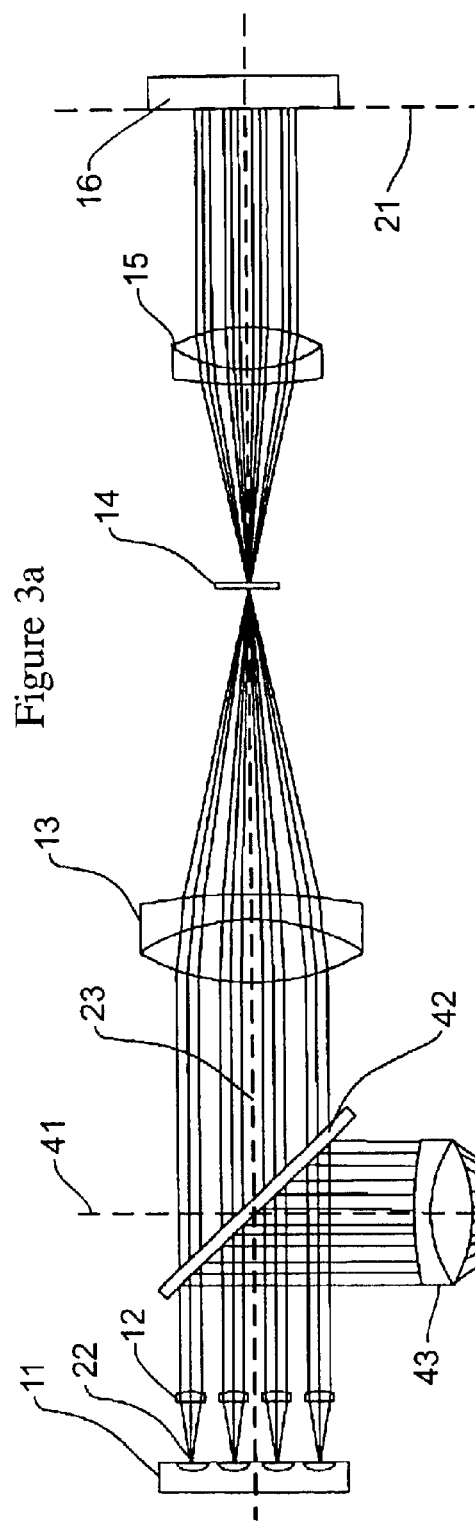
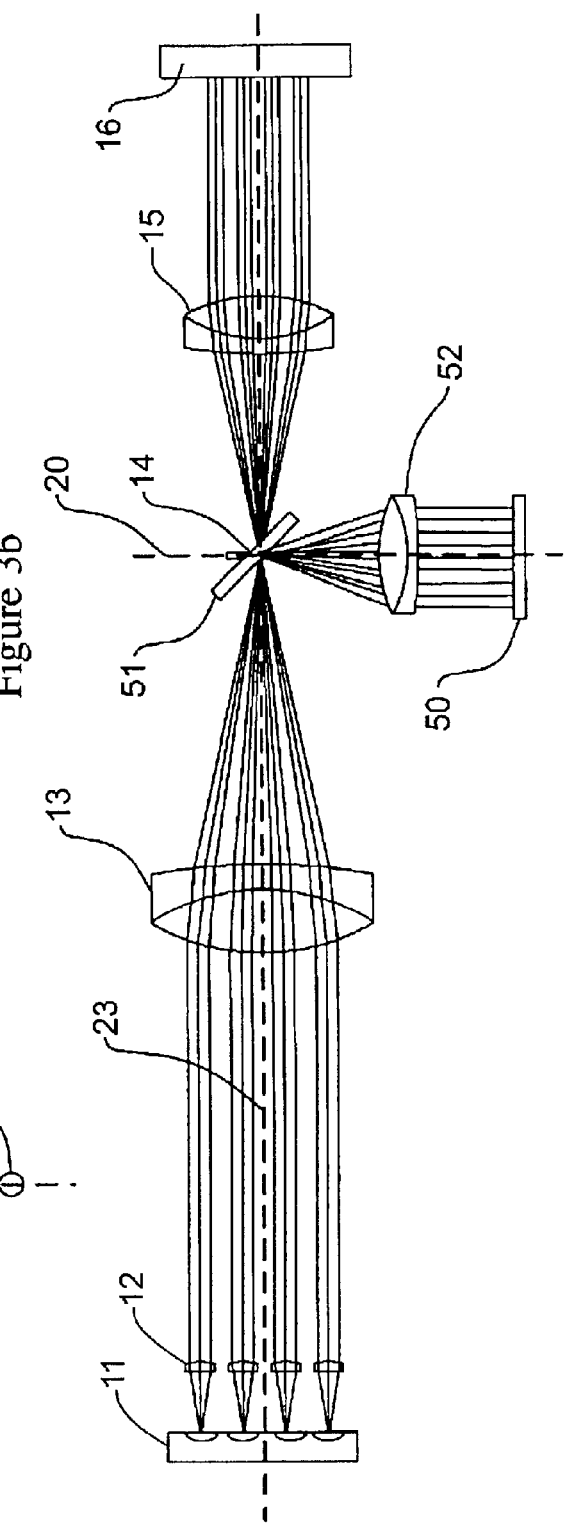
Figure 3a
Figure 3b

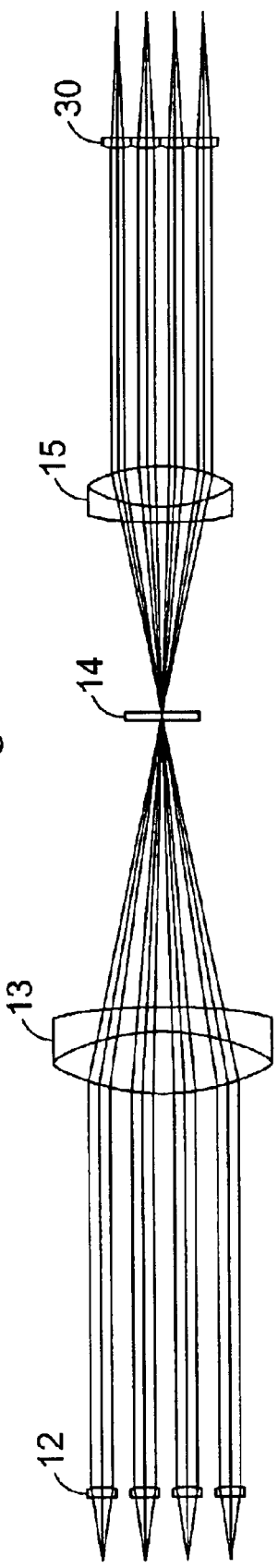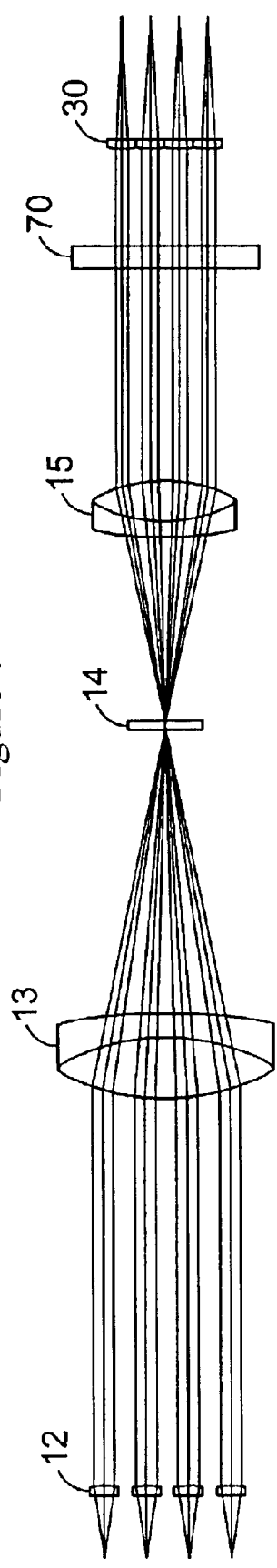

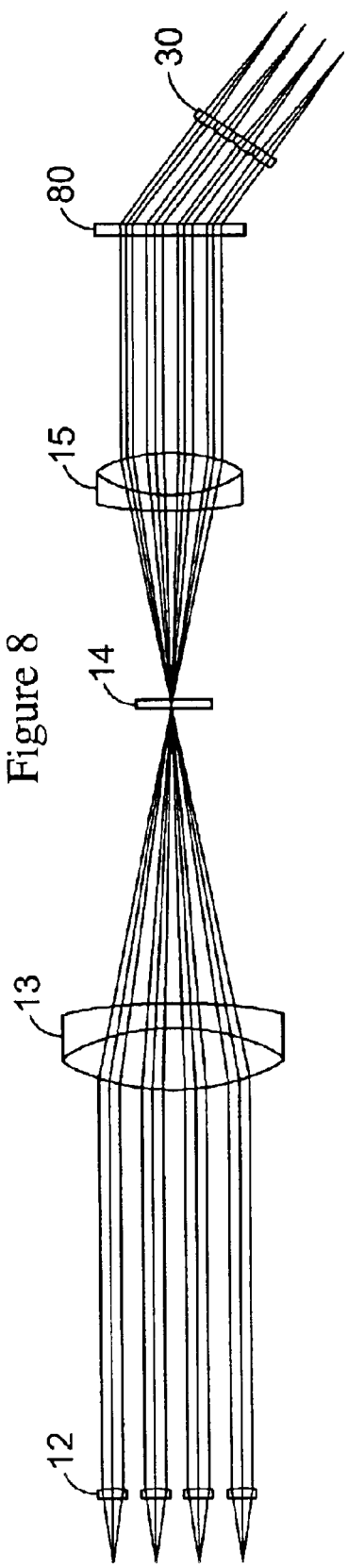
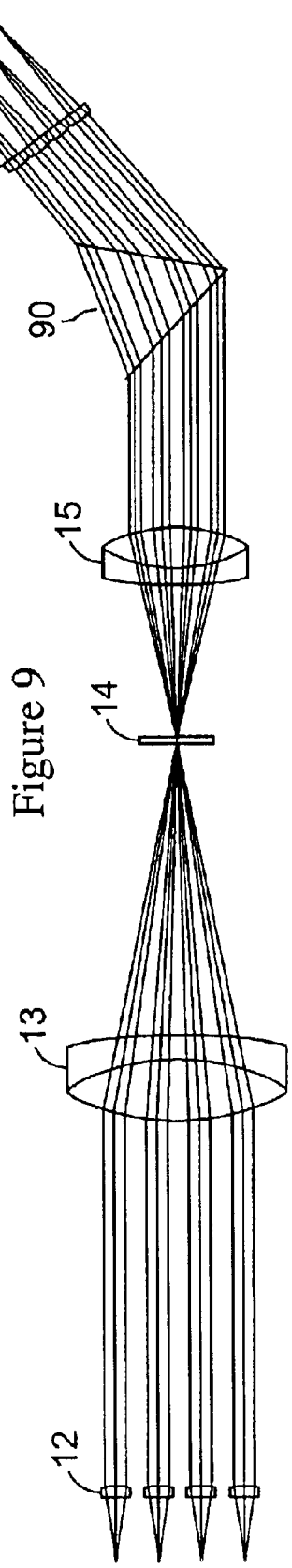
Figure 8
Figure 9

IMAGING SYSTEM AND METHOD FOR REDUCTION OF INTERSTITIAL IMAGES

CROSS REFERENCE TO RELATED APPLICATIONS

This application claims a priority benefit under 35 U.S.C. § 119(e) from U.S. patent application No. 60/379,483, filed May 10, 2002, which is incorporated herein by reference.

FIELD

The present teachings relate generally to imaging systems and methods and more particularly to an optical imaging systems for close-packed imaging of interstitially-spaced samples.

INTRODUCTION

Frequently, for example in molecular biology, it is desirable to view or otherwise image individual samples, in order to observe or otherwise detect changes in the physical state of the sample. Various optical imaging systems that measure photon flux emitted by samples have been developed. These systems typically comprise groups of lenses to create an image on a charge-coupled display or similar imaging device.

One problem with imaging systems among those in the art is the presence of interstitial space in the images created. Interstitial space (also known as "dead space") is the blank area between samples, or the blank space between the images of the samples. In many instances, the interstitial space between samples is proportionally larger in size than the samples themselves. The presence of interstitial space between the images of the samples can decrease the overall efficiency of the imaging system, for example wasting the capacity of the detector and reducing image quality. Additionally, the throughput of the imaging system (i.e., the number of samples that can be processed in a timely fashion) can be reduced.

It is desirable to remove or reduce interstitial space between the images of the samples. Such removal or reduction can provide more resolution for the images of a given number of samples, more images of samples on a detector of a given capacity, or less area on a detector for images of a given number of samples.

SUMMARY

According to various embodiments, an imaging system can comprise a plurality of collection lenses, each lens of the plurality of collection lenses positioned to receive and collimate light from a plurality of samples corresponding to the collection lenses; a first lens system positioned to receive the collimated light from the plurality of collection lenses and focus the collimated light on a primary imaging plane; a second lens system positioned to receive and collimate light from the primary imaging plane; a field stop positioned at the primary imaging plane to block at least a portion of light from dead space between the plurality of samples; and a detector positioned to detect light from the second lens system.

According to various embodiments, an imaging system can comprise two or more samples, wherein the samples have a first dead space between them; a first lens system comprising a first focal length; a second lens system comprising a second focal length; a field stop positioned between the first lens system and the second lens system; and a detector, wherein images of the objects are detected, wherein the images have a second dead space between them; wherein the first lens system, the field stop, and the second lens system are positioned between the sample and the detector; and wherein the second dead space is less than the first dead space by a factor of second focal length divided by the first focal length.

According to various embodiments, a method for imaging can comprise providing two or more spaced objects, wherein the objects have a first dead space between them; positioning a field stop between a first lens system and a second lens system; and providing a detector, wherein images of the objects are detected, wherein the images have a second dead space between them; wherein the first lens system, the field stop, and the second lens system are positioned between the object and the detector; and wherein the second dead space is less than the first dead space.

According to various embodiments, a method for imaging can comprise collimating light collected from a plurality of samples spaced on a sample holder; focusing the collimated light onto a primary image plane; re-collimating the light; and detecting light from each of the plurality of samples, wherein light from the plurality of samples is substantially detected while at least a portion of light from dead space between the plurality of samples is blocked.

Further embodiments and advantages of the present teachings are discussed below with respect to the following figures. It should be understood that the embodiments described herein are examples of the present teachings and are intended for purposes of illustration only and are not intended to limit the scope of the teachings.

BRIEF DESCRIPTION OF THE DRAWINGS

According to various embodiments, imaging systems are illustrated in FIGS. 1–10.

FIG. 3 shows a schematic diagram illustrating various embodiments, comprising a optional illumination source.

FIG. 6 shows a schematic diagram illustrating various embodiments, without a chromatic separation device.

FIG. 7 shows a schematic diagram illustrating various embodiments, comprising a bandpass filter.

FIG. 8 shows a schematic diagram illustrating various embodiments, comprising a diffraction grating.

FIG. 9 shows a schematic diagram illustrating various embodiments, comprising a prism.

It should be noted that the diagrams set forth in these Figures are intended to show the general characteristics of imaging systems in accordance with the present teachings, for the purpose of the description of such embodiments herein. These diagrams are not drawn to scale, may not precisely reflect the characteristics of any given embodiment, and are not necessarily intended to define or limit specific embodiments within the scope of this invention.

DESCRIPTION OF VARIOUS EMBODIMENTS

According to various embodiments, the imaging system provides high resolution imaging of objects on a platform for use in molecular biology. The imaging system provides an apparatus that reduces the dead space between the images of the objects formed on a detector.

According to various embodiments, the imaging system can comprise a sample holder, two imaging lenses, two or more collection lenses, a field stop, and a detector. The samples can be distributed on a sample holder in a variety of ways. Samples can include any material of interest in research, including biological materials (such as tissue cells, DNA segments, and other genetic materials), and chemical samples (such as enzymes and other proteins, peptides, and small molecules, such as from a chemical library, and other chemical samples). (As used herein, the word "include" and its variants are intended to be non-limiting, such that recitation of items in a list is not to the exclusion of other like items that may also be useful in the materials, compositions, devices, and methods of the present teachings.) The sample holder can comprise any structure suitable for affixing, containing, holding or otherwise presenting two or more samples in such a manner that they can be imaged. A sample holder can comprise structures including containers, holders, wells or other devices that are capable of presenting an individual sample in such a manner that it can be imaged. The samples holder can be constructed of any materials, including at least one of glass, plastic, and composites.

Figure 5A:
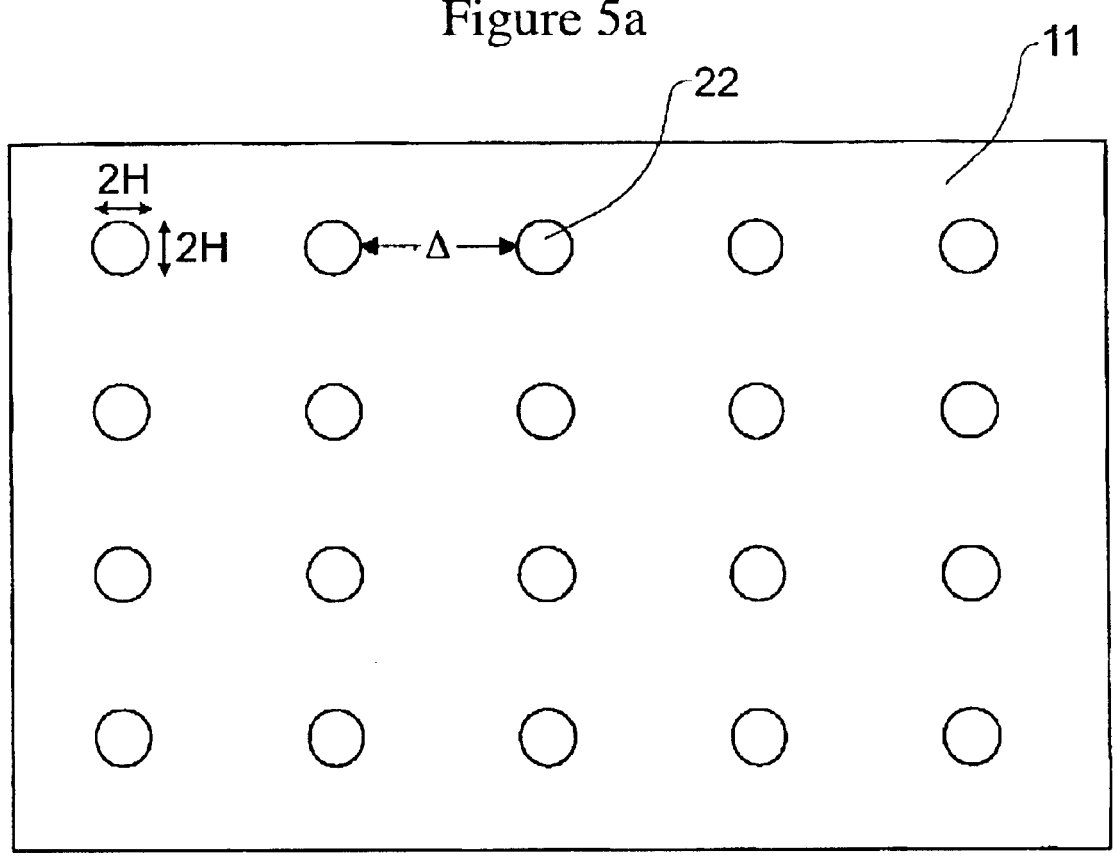
FIG. 5a shows a perspective view of object regions on a substrate according to various embodiments.

According to various embodiments, the samples on the sample holder can be disposed in a regular matrix, such that the distance between each sample along the x-axis and y-axis of the sample holder (i.e., in the plane of the platform perpendicular to the optical axis of the first imaging lens) can be similar, as illustrated in FIG. 5a. For example, the sample holder can be a standard 96-well reaction plate. According to various embodiments, the sample holder can comprise an irregular matrix, where the x-axis dead space is not equal to the y-axis dead space. According to various embodiments, the sample holder can be formed to accommodate any collection of samples positioned in any fashion, including rectilinear or curvilinear, as long as the position is known so that the collection lenses can be positioned to correspond to the samples.

According to various embodiments, the light provided to the imaging system can be reflected light, including light from a source reflected by the sample or components of the imaging system, scattered light, including light scattered by the sample or components of the imaging system, chemiluminescent light, electroluminescent light, and/or fluorescent light, including light emitted by the sample.

According to various embodiments, the imaging system comprises various lenses and other optical surfaces oriented to project images of the samples on a detector. Lenses and other optical surfaces among those useful herein are known in the art and are made of various materials including glass (for example, optical glass), quartz, fluorite, rock salt, plastic, and composites. Optical surfaces, including those of lenses, according to the present teachings can be coated as known in the art to optimize light reflected or transmitted through the surface of the lenses. As further referenced herein, each lens has an object space (which is the spatial region along the optical axis of the lens containing the source of light reflected, scattered, and/or emitted from a sample), and an image space (which is the spatial region along the optical axis of the lens that is opposite of the object space). Each lens has a focal point and focal plane (the plane perpendicular to the optical axis of the lens in which the focal point is located). Each lens in the system also has an image plane and object plane which may, or may not, in the system coincide with the focal planes of the lens. Concepts among those underlying the optical devices useful herein are described in F. Jenkins and H. White, *Fundamentals of Optics*, 4$^{th}$ ed. (McGraw Hill 1976), incorporated by reference herein.

According to various embodiments, the imaging system can comprise any of a variety of lens types. The lenses can be converging, or positive lenses, which are thicker in the center (along their optical axis) than at their edges. Such lenses include equiconvex, plano-convex, and positive meniscus lenses. The lenses may be single lenses, doublets, or other compound lenses. The lenses can be Fresnel lenses, hemispherical lenses, hyper-hemispherical lenses, and/or spherical lenses.

Figure 1:
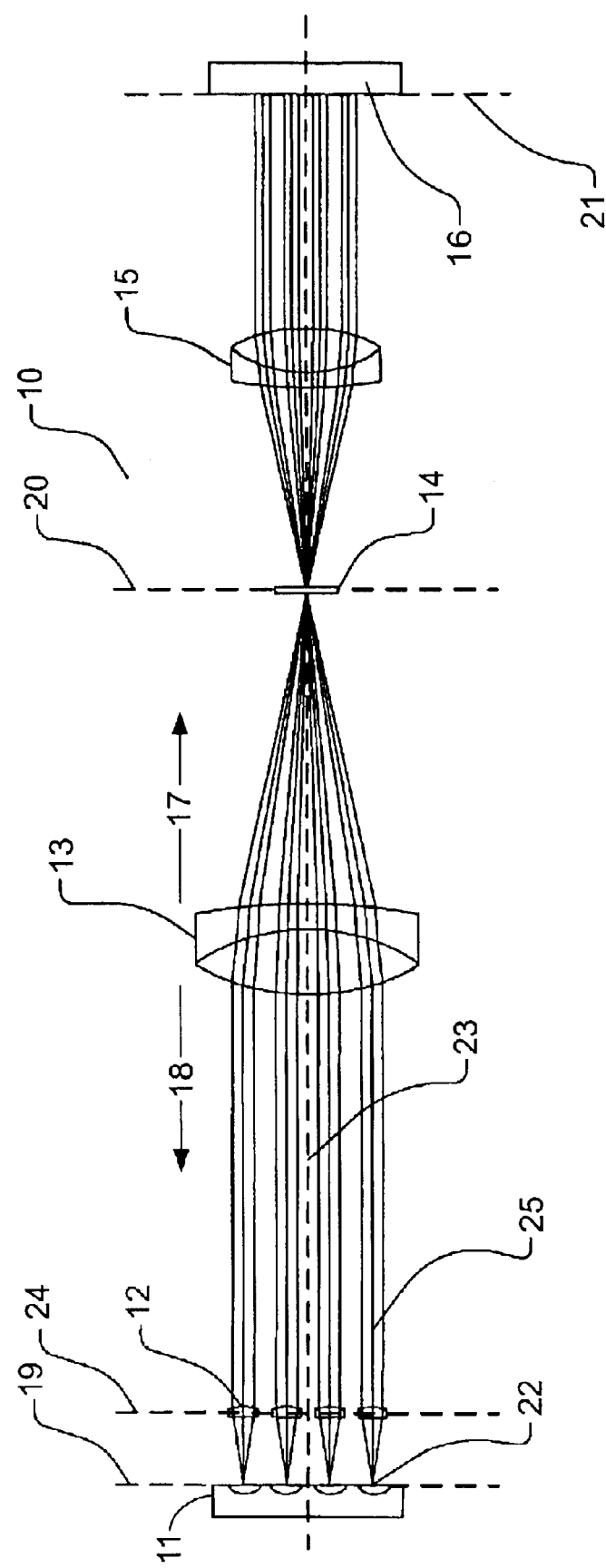
FIG. 1 shows a schematic diagram illustrating various embodiments.

According to various embodiments, FIG. 1 illustrates imaging system (10) comprising a first lens system (13), a second lens system (15), two or more collection lenses (12), a field stop (14), and a detector (16). According to various embodiments, the first lens and/or second lens can be a cemented achromatic doublet. The field stop, second imaging lens, and detector can be in the image space (17) of the first lens (13). The sample holder (11) and the collection lenses (12) can be in the object space (18) of the first lens (13). Primary object plane (19) can define the physical plane of the samples. Primary intermediate image plane (20) can define the visual plane wherein the images of the samples converge. According to various embodiments, the field stop (14) can be positioned at the primary intermediate image plane (20) of the imaging system. Primary image plane (21) can define a visual plane wherein the light transmissions can be received by the detector (16), and images of the samples can be projected.

According to various embodiments, the sample holder (11) comprises a plurality of sample (22) that can be positioned in the object space (18) of the first lens system (13). According to various embodiments, the second lens system (15) can be substantially coaxial with the first lens system (13) (i.e., they have a common optical axis or optical axes that are substantially the same).

Figure 10:
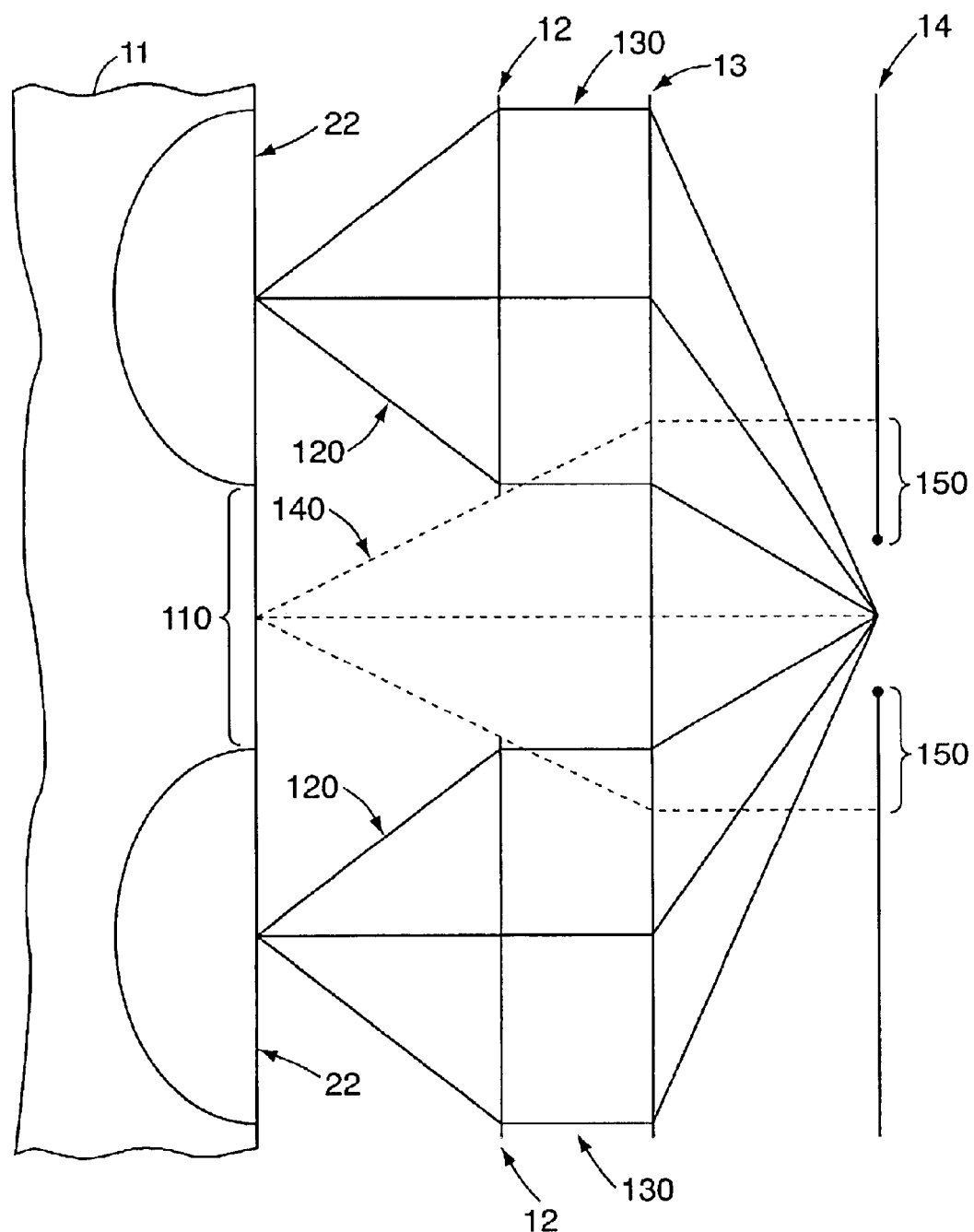
FIG. 10 shows a schematic diagram illustrating various embodiments, with lines representing optical components to show the cropping effect of the field stop.

According to various embodiments, two or more collection lenses (12) can be positioned in the object space (18) of the first lens system (13). The collection lenses can be molded aspheres. The number of collection lenses (12) present in the imaging system can be proportionate to, equal to, or substantially equal to the number of samples (22) present in one image of the sample holder (11). The collection lenses can be positioned in a plane substantially perpendicular to the primary axis (23) which can be the optical axis of the first lens system. The collection lenses can be symmetrically oriented around the primary axis (23). For example, imaging systems comprising an odd number of collection lenses (12), one collection lens can be coaxial with the primary axis (23), and the other collection lenses can be positioned in collection plane (24) symmetrically from the primary axis (23) along one or more axes parallel to the primary axis (23). For example, imaging systems comprising an even number of collection lenses (12), as illustrated in FIG. 1, the collection lenses can be positioned symmetrically from the primary axis (23) along one or more axes parallel to the primary axis (23). According to various embodiments, collection lenses (12) can be distributed as needed to collect light from samples (22) without regard to the distribution of collection lenses (12) around primary axis (23). According to various embodiments, as illustrated in FIG. 10, collection lenses (12) can provide collimated light (130) originating from objects (22). Collimated light (130) can be parallel with primary axis (23). According to various embodiments, collection lenses (12) can be positioned in collection plane (24) that can be perpendicular to primary axis (23). According to various embodiments, collection lenses (12) can be positioned to provide collimated light (130) parallel to primary axis (23).

According to various embodiments, imaging system (10) comprises a field stop (14). The field stop can be positioned between the first lens system (13) and the second lens system (15). The field stop can be positioned at primary intermediate image plane (20). According to various embodiments, primary intermediate plane image (20) can be the focal plane of the first lens system (13). According to various embodiments, field stop (14) can be positioned at a plane that is the common focal plane of the first lens system (13) and second lens system (15). The field stop (14) can be configured to have a size and shape to block light rays emanating from the dead space between samples (22) on sample holder (11).

According to various embodiments, the field stop can comprise any opening that passes light emanating from the samples while blocking at least some of the light emanating from the dead space between the samples. According to various embodiments, the field stop can be a spatial filter. According to various embodiments, the field stop can be a slit comprising two substantially parallel edges. According to various embodiments, the field stop can be the shape of a square or other parallelogram. According to various embodiments, the field stop can be curved, circular, oval, and/or elliptical. According to various embodiments, the field stop can be a pin hole.

According to various embodiments, as illustrated in FIG. 1, imaging system (10) can be characterized as having a plurality of optical channels (25). Each optical channel (25) comprises the optics for transmission of light from each sample (22) onto detector (16). Thus, the number of optical channels (25) is equal to the number of samples (22) imaging system (10) can image. Image (200) on detector (16) can be characterized as comprising a group or bundle of light rays originating from a single sample. Each optical channel (25) can comprise one of the collection lenses (12), the first lens system (13), the field stop (14), and the second lens system (15). According to various embodiments, a light bundle from each sample (22) can travel through and can be collimated by one of the collection lenses (12). The bundle then travels through first lens system (13) and can be focused onto primary intermediate image plane (20) where the field stop (14) is positioned. After exiting the field stop (14), each of the light bundles can travel to the second lens system (15), and can be collimated as they pass to detector (16).

Figure 2:
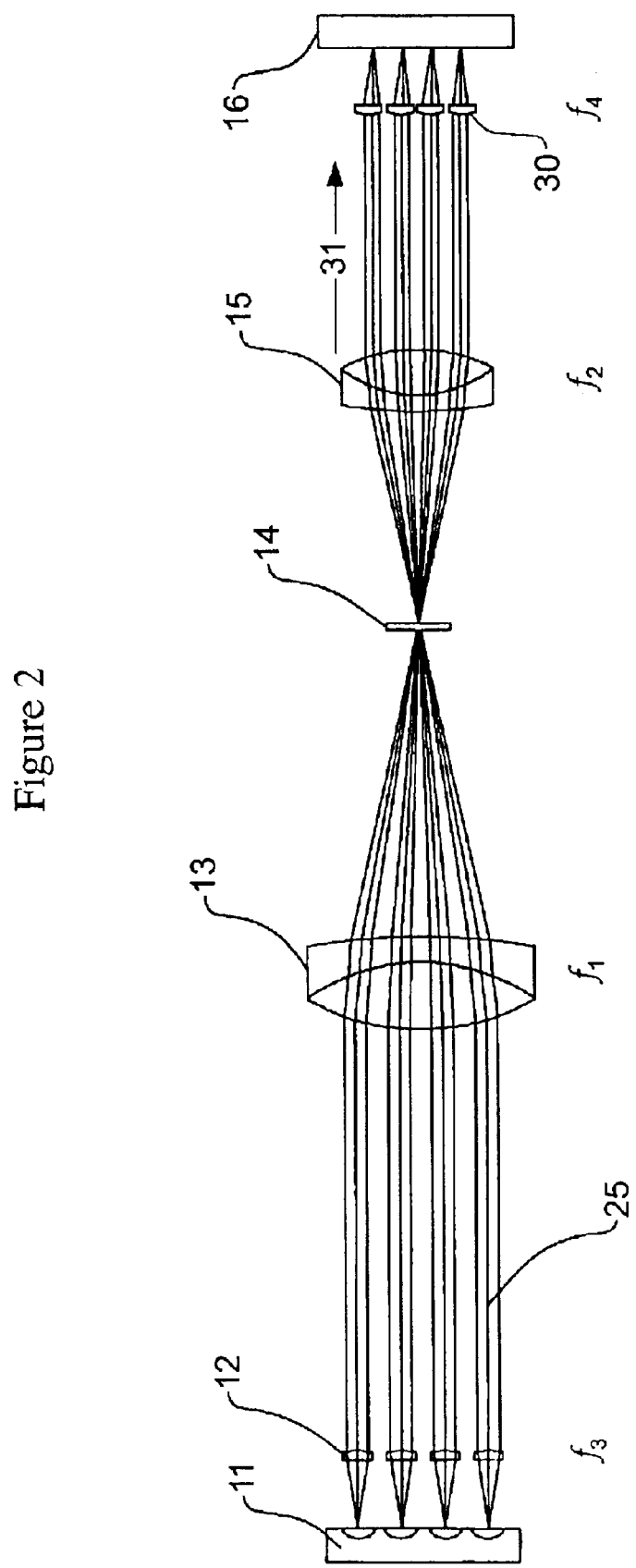
FIG. 2 shows a schematic diagram illustrating various embodiments, comprising a plurality of optional focusing lenses.

According to various embodiments, the imaging system can comprise optical components that enhance or otherwise affect the manner in which the image is formed, transmitted or detected. Such optical elements include lenses, mirrors, light sources, filters, dispersive elements, and detectors. As illustrated in FIG. 2, various embodiments can comprise two or more focusing lenses (30) in image space (31) of the second lens system (15), between second lens system (15) and detector (16). Each focusing lens (30) can form an image (200) of sample (22) onto detector (16). Without the focusing lenses (30), the collimated beams from second lens system (15) can be projected onto detector (16) as an array of light beams, as illustrated in FIG. 1. The focusing lenses (30) can focus the image (200) of sample (22) on detector (16). As illustrated in FIG. 2, each of the optical channels (25) of the imaging system (10) can comprise one of collection lenses (12), first lens system (13), field stop (14), second lens system (15), and one of focusing lenses (30).

According to various embodiments, the optical imaging system can comprise a light source, for illuminating the samples in the sample holder. As illustrated in FIG. 3a, imaging system (10) can comprise optical components for illuminating samples along primary axis (23). Light source (40) can be positioned along an axis (41) that intersects with, and can be substantially perpendicular to, primary axis (23). FIG. 3a illustrates beam splitter (42), including a dichroic mirror, positioned in the region of collimated light (130) between collection lenses (12) and first lens system (13). A collimating lens (43) can be positioned between light source (40) and beam splitter (42). Beam splitter (42) can be a dichroic reflective surface or mirror that can reflect light at a wavelength illuminated by light source (40) toward samples (22), and can transmit light emitted at a different wavelength from samples (22) to the remaining components of the imaging system (10).

According to various embodiments, illumination can be positioned at other points in the system. For example, illumination can be positioned to intersect at primary intermediate image plane (20) wherein field stop (14) can be positioned. As illustrated in FIG. 3b, illumination source (50) can be positioned along the primary intermediate image plane (20) or an axis parallel that is substantially perpendicular to the primary axis (23). Illuminating light can enter the primary axis (23) at beam splitter (51) positioned in front of, at, or beyond the primary intermediate image plane (20). Illuminating light can converge to a focus that is conjugate to the primary intermediate image plane. The field stop (14) can be positioned at the primary intermediate image plane (20) coincident with the beam splitter (51). According to various embodiments, illumination source (50) can be collimated, for example a laser light source. Third lens system (52) can be positioned along the axis of the illumination (19), between illumination source (50) and beam splitter (51) to focus the collimated light.

Figure 4:
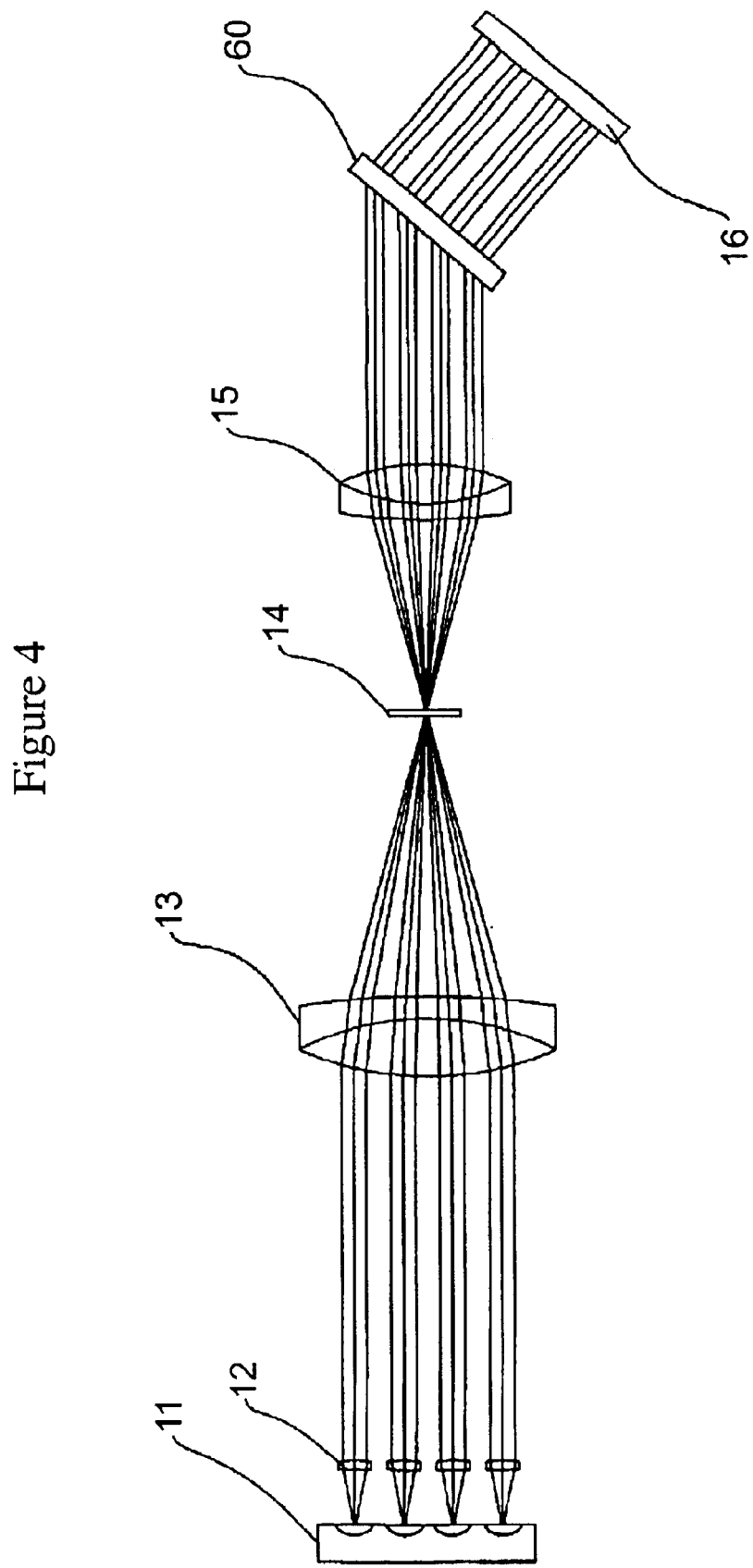
FIG. 4 shows a schematic diagram illustrating various embodiments, comprising a wavelength separation element.

According to various embodiments, the imaging system can comprise a chromatic separation component for modifying the spectral properties of the images of the samples. Such a chromatic separation component can include filter wheels, prisms, gratings, or various other dispersive and filtering elements. The chromatic separation device can separate the light from the image into its spectral components. The chromatic separation device can operate via dispersion, diffraction, and/or filtering. FIG. 4 illustrates an imaging system comprising a chromatic separation component (60) between second lens system (15) and detector (16). FIG. 6 illustrates an imaging system comprising focusing lenses (30) without a chromatic separation component. FIG. 7 illustrates an imaging system comprising a bandpass filter (70) as a chromatic separation component positioned between second lens system (15) and focusing lenses (30). A filter component, such as bandpass filter (70), can provide specific wavelengths of light to the detector (not shown) while filtering out others to provide chromatic separation. FIG. 8 illustrates an imaging system comprising a grating (80) as a chromatic separation device positioned between second lens system (15) and focusing lenses (30). A diffractive component, such as grating (80), can provide diffraction to the light from second lens system (15) to provide chromatic separation. Focusing lenses (30) can be positioned to focus specific wavelengths of light onto the detector (not shown). FIG. 9 illustrates an imaging system comprising a prism (90) as a chromatic separation device positioned between second lens system (15) and focusing lenses (30). A dispersive component, such as prism (80), can provide dispersion to the light from second lens system (15) to provide chromatic separation. Focusing lenses (30) can be positioned to focus specific wavelengths of light to the detector (not shown). According to various embodiments, imaging systems using gratings or prisms for color separation can provide spatial information in one dimension on the detector and spectral information in the other dimension.

According to various embodiments, the imaging system can remove or reduce dead space between the images of the samples. Such removal or reduction can provide increased resolution for the images of a given number of samples, more images of samples on a detector of a given capacity, or less area on a detector for images of a given number of samples. According to various embodiments, the detector can be a charged-coupled device (CCD) or other pixilated image sensor. As known in the art, CCD detectors comprise pixels for imaging. The imaging area of the CCD detector can provide a number of pixels. According to various embodiments, removing or reducing the dead space imaged on the CCD detector can provide additional pixels for increasing resolution for the images of a given number of samples, i.e., dedicating more pixels per sample image. According to various embodiments, removing or reducing the dead space imaged on the CCD detector can provide additional pixels for imaging more samples on the pixels provided by the CCD detector. According to various embodiments, removing or reducing the dead space imaged on the CCD detector can provide surplus pixels justifying the use of a CCD detector with a smaller imaging area that provides less pixels.

Figure 5B:
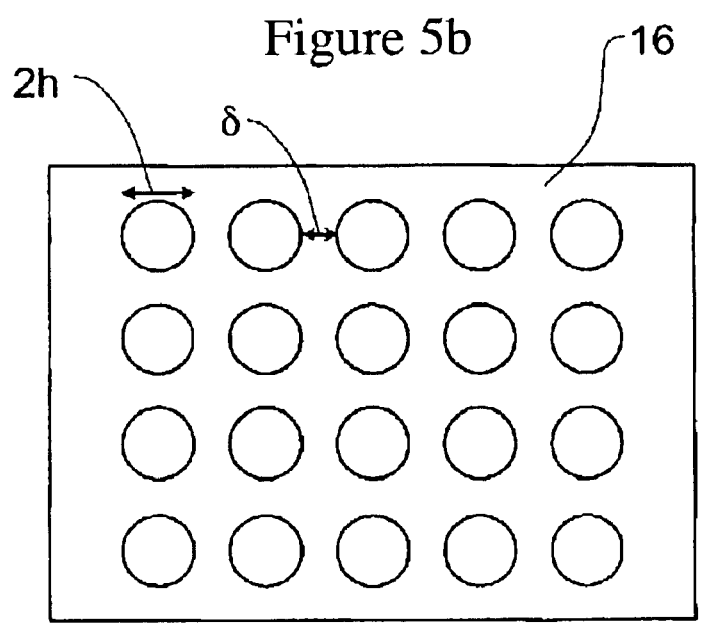
FIG. 5b shows a perspective view of image regions formed on a detector according to various embodiments.

According to various embodiments, FIG. 5a illustrates a top view of sample holder (11) comprising a plurality of samples (22). Each sample to be imaged can have a 2H by 2H dimension. The samples (22) can be positioned a certain distance apart, represented by the value, Δ. The value, Δ, is known as interstitial space or dead space (110) between each sample (22) to be imaged. According to various embodiments, the value, Δ, can be much larger than 2H. According to various embodiments, an imaging system comprising collection lenses, a first lens system, a field stop, and a second lens system can reduce the interstitial space or dead space between the images (200) of the samples projected on detector (16) to the value, δ, where δ is less than Δ. According to various embodiments, an imaging system comprising collection lenses, a first lens system, a field stop, and a second lens system can reduce the dimensions of the images (200) of the samples to 2h by 2h. FIG. 5b illustrates detector (16) where the dead space between images (200) of samples can be δ and the dimension of images (200) of samples can be 2h. The imaging system can provide a ratio δ/Δ that is less than the ratio h/H. It should be noted that the values of H, Δ, h, and δ can vary, depending on the sample holder, the specific samples to be imaged, and the optical components of the imaging system.

According to various embodiments, each of the lenses of the imaging system can be characterized by their focal lengths. FIG. 2 illustrates an imaging system comprising collection lenses (12) wherein each can have a focal length, $f_3$, first lens system (13) that can have a focal length, $f_1$, second lens system (15) that can have a focal length, $f_2$, and focusing lenses (30) wherein each can have a focal length, $f_4$. The combination and orientation of these lenses can determine the amount of reduction in the dead space between the images of the samples.

According to various embodiments, an imaging system can accommodate the dead space (110) between each of the samples (22) that can have a value of Δ by providing lenses with focal lengths that can provide a desired amount of dead space reduction between the images (200) of samples. The dead space between the images (200) of samples on the detector (16) that can have a value of δ that relates to the dead space (110) between the samples (22) that can have the value Δ according to the ratio of $f_2$ to $f_1$, according to formula (A):

$$\delta = \frac{f_2}{f_1}\Delta \quad (A)$$

According to various embodiments, an imaging system can provide reduction in the dimensions of images (200) of samples represented by h can be reduced by a ratio function of $f_1$ through $f_4$. The imaging system can modify the dimension of samples (22) represented by H to the dimension of the images (200) of the samples represented by h according to formula (B):

$$h = \frac{f_1 \times f_4}{f_2 \times f_3}H \quad (B)$$

According to various embodiments, an imaging system can comprise a field stop to reduce the dead space between the images (200) of the samples. The field stop blocks the dead space around the images of the samples to reduce or eliminate the dead space between the images (200) of the samples. The field stop blocks the dead space between the images (200) of the samples according formula (A). As illustrated in FIG. 10, samples (22) from samples holder (11) can provide light (120) that can be collimated by collection lenses (12) to form collimated light (130). Collimated light (130) can be focused by first lens system (13) onto the opening of field stop (14). Dead space (110) between samples (22) can provide light (140). Light (140) can avoid collection lenses (12) and can avoid being collimated. Light (140) that is not collimated can avoid being focused onto the opening of field stop (14) and can be blocked portions (150) of field stop (14). The field stop (14) can thereby reduce light (140) from dead space (110) between samples (22) that can reach the detector. According to various embodiments, light (140) can be blocked by a mask corresponding to the gaps between collection lenses and can avoid being focused onto the opening of field stop (14).

According to various embodiments, it is desirable to avoid superimposing the dead space surrounding one sample on the image of the adjacent sample and vice versa. The field stop can reduce cross-over of the images of the samples.

According to various embodiments, a method for imaging can comprise providing two or more samples, wherein the samples have a first dead space between them; positioning a field stop between a first lens system and a second lens system; and providing a detector, wherein images of the samples are detected, wherein the images have a second dead space between them; wherein the first lens system, the field stop, and the second lens system are positioned between the samples and the detector; and wherein the second dead space is less than the first dead space. The method can further comprise positioning the first lens system and the second lens system such that both their image planes coincide with the field stop.

According to various embodiments, a method for imaging can comprise collimating light collected from a plurality of samples spaced on a sample holder; focusing the collimated light onto a primary image plane; re-collimating the light; and detecting light from each of the plurality of samples, wherein light from the plurality of samples is substantially detected while at least a portion of light from dead space between the plurality of samples is blocked. The method can further comprise spatially filtering light near the primary image plane. The term "near" as used herein refers to at or substantially proximate to the plane.

EXAMPLE

According to various embodiments, the dimensions and materials associated with an example of the optical imaging system are described in the following Table 1. Table 1 describes the positioning and features of the optical elements. Optical elements are defined in order in the system, from object to detector, including distances between elements.

TABLE 1

| Optical Element | Curvature radius (mm) | Aperture Radius (mm) | Material | Distance to next component/ surface (mm) |
|---|---|---|---|---|
| object | — | 100 | — | 13.72 |
| collection lens surface 1 | 0 | 3.00 | CO550 | 2.20 |
| collection lens surface 2 | −9.13 | 3.00 | — | 89.55 |
| first lens surface 1 | 47.90 | 23.25 | BAK4 | 13.5 |
| first lens surface 2 | −41.60 | 23.25 | SF10 C | 5.25 |
| first lens surface 3 | −129.63 | 23.25 | — | 64.53 |
| field stop | — | 25.00 | air | 43.02 |
| second lens surface 1 | 86.43 | 15.50 | SF10 C | 3.50 |
| second lens surface 2 | 27.73 | 15.50 | BAK4 | 9.00 |
| second lens surface 3 | −31.94 | 15.50 | — | 70.50 |
| focusing lens surface 1 | 18.26 | 2.65 | CO550 | 2.20 |
| focusing lens surface 2 | 0 | 3.00 | — | 29.37 |
| detector | — | — | — | — |

Table 1 describes an imaging system comprising a collection lens, a first lens system, a field stop, a second lens system, and a focusing lens between the sample and the detector. The collection lens is a piano-convex lens, the first imaging lens is a cemented doublet, the second imaging lens is a cemented doublet, and the focusing lens is a plano-convex lens. The last column in Table 1, Distance to next component/surface in millimeters represents distances between optical components (e.g., 13.72 mm between the sample and the first surface of the collection lens), or distance between surfaces of a lens (i.e., thickness of lens; e.g., the collection lens is 2.20 mm thick). The rest of Table 1 describes the curvature radius in millimeters (i.e. positive values represent curvature towards the detector and negative values represent curvature towards the sample), the aperture radius (e.g. the radius of the lens or the length of the field stop), and the material composition of the optical components through which light passes.

The example and other embodiments described herein are exemplary and not intended to be limiting in describing the full scope of optical systems of this invention. Equivalent changes, modifications and variations of specific embodiments, materials, compositions and methods may be made within the scope of the present invention, with substantially similar results.

For the purposes of this specification and appended claims, unless otherwise indicated, all numbers expressing quantities, percentages, or other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a lens" includes two or more lenses.

What is claimed is:

1. A system for imaging, comprising:
   two or more samples, wherein the samples have a first dead space between them;
   a first lens system comprising a first focal length;
   a second lens system comprising a second focal length;
   a field stop positioned between the first lens system and the second lens system; and
   a detector, wherein images of the objects are detected, wherein the images have a second dead space between them;
   wherein the first lens system, the field stop, and the second lens system are positioned between the sample and the detector; and
   wherein the second dead space is less than the first dead space by a factor of second focal length divided by the first focal length.

2. A system according to claim 1, wherein the field stop is in an image plane of the first lens system.

3. A system according to claim 2, wherein the field stop is in an image plane of the second lens system.

4. A system according to claim 3, further comprising two or more collection lenses positioned between the first imaging lens and the objects, wherein each collection lens has a third focal length.

5. A system according to claim 4, further comprising two or more focusing lenses positioned between the second imaging lens and the detector, wherein each focusing lens has a fourth focal length.

6. A system according to claim 5, wherein the images of the objects are reduced in size by a factor of the first focal length and the fourth focal length both divided by the second focal length and the third focal length.

7. A method for imaging, comprising:
  providing two or more spaced samples, wherein the samples have a first dead space between them;
  positioning a field stop between a first lens system and a second lens system; and
  providing a detector, wherein images of the samples are detected, wherein the images have a second dead space between them;
  wherein the first lens system, the field stop, and the second lens system are positioned between the samples and the detector; and
  wherein the second dead space is less than the first dead space.

8. A method according to claim 7, further comprising positioning the first lens system and the second lens system such that both their image planes coincide with the field stop.

9. An imaging system, comprising:
  a plurality of collection lenses, each lens of the plurality of collection lenses positioned to receive and collimate light from a plurality of samples corresponding to the collection lenses;
  a first lens system positioned to receive the collimated light from the plurality of collection lenses and focus the collimated light on a primary imaging plane;
  a second lens system positioned to receive and collimate light from the primary imaging plane;
  a field stop positioned at the primary imaging plane to block at least a portion of light from dead space between the plurality of samples, wherein the field stop is in an image plane of the first lens system and the second lens system;
  a detector positioned to detect light from the second lens system; and
  a chromatic separation device positioned between the second lens system and the detector, wherein the chromatic separation device comprises at least one of a bandpass filter, a grating, and a prism.

10. An imaging system, comprising:
  a plurality of collection lenses, each lens of the plurality of collection lenses positioned to receive and collimate light from a plurality of samples corresponding to the collection lenses;
  a first lens system positioned to receive the collimated light from the plurality of collection lenses and focus the collimated light on a primary imaging plane;
  a second lens system positioned to receive and collimate light from the primary imaging plane;
  a field stop positioned at the primary imaging plane to block at least a portion of light from dead space between the plurality of samples;
  a detector positioned to detect light from the second lens system; and
  a mask corresponding to gaps between the plurality of collection lenses.

* * * * *